United States Patent [19]
Bush et al.

[11] Patent Number: 5,674,272
[45] Date of Patent: Oct. 7, 1997

[54] CRUSH RESISTANT IMPLANTABLE LEAD

[75] Inventors: M. Elizabeth Bush; Craig E. Mar, both of Fremont; Peter A. Altman, San Francisco; Paul M. Paspa, Santa Clara, all of Calif.

[73] Assignee: Ventritex, Inc., Sunnyvale, Calif.

[21] Appl. No.: 465,155

[22] Filed: Jun. 5, 1995

[51] Int. Cl.$^6$ .................................................. A61N 1/375
[52] U.S. Cl. ........................ 607/122; 607/116; 128/642
[58] Field of Search ................................ 607/116, 122, 607/119, 117, 118, 120, 121, 123–133, 5, 37; 128/642

[56] References Cited

U.S. PATENT DOCUMENTS

| | | | |
|---|---|---|---|
| 3,405,715 | 10/1968 | Hagfors | 607/118 |
| 3,572,344 | 3/1971 | Bolduc . | |
| 3,724,467 | 4/1973 | Avery et al. | 607/117 |
| 3,788,329 | 1/1974 | Friedman | 607/122 |
| 4,422,460 | 12/1983 | Pohndorf | 607/125 |
| 4,469,104 | 9/1984 | Peers-Trevarton | 128/419 |
| 4,573,480 | 3/1986 | Hirschberg | 607/119 |
| 4,603,705 | 8/1986 | Speicher et al. | 607/122 |
| 4,608,986 | 9/1986 | Beranek et al. | 607/123 |
| 4,630,611 | 12/1986 | King | 128/642 |
| 4,954,105 | 9/1990 | Fischer | 607/122 |
| 5,007,422 | 4/1991 | Pless et al. | 28/419 |
| 5,007,435 | 4/1991 | Doan et al. | 128/784 |
| 5,044,375 | 9/1991 | Bach, Jr. et al. | 128/786 |
| 5,095,903 | 3/1992 | DeBellis | 607/129 |
| 5,246,014 | 9/1993 | Williams et al. | 607/122 |
| 5,324,321 | 6/1994 | Pohndorf et al. | 607/116 |
| 5,330,523 | 7/1994 | Campbell et al. | 607/122 |
| 5,358,516 | 10/1994 | Myers et al. | 607/116 |
| 5,466,252 | 11/1995 | Soukup et al. | 607/116 |
| 5,466,253 | 11/1995 | Doan | 607/122 |
| 5,476,497 | 12/1995 | Mower et al. | 607/122 |
| 5,545,203 | 8/1996 | Doan | 607/122 |
| 5,584,873 | 12/1996 | Shoberg et al. | 607/122 |

OTHER PUBLICATIONS

"Anatomical and Morphological Evaluation of Pacemaker Lead Compression", Jacobs, et al., PACE, vol. 16, Part I, Mar. 1993, pp. 434–444.

"Anatomical Mechanisms Explaining Damage to Pacemaker Leads, Defibrillator Leads, and Failure of Central Venous Catheters Adjacent to the Sternoclavicular Joint", Magney, et al., PACE, vol. 16, Part I, Mar. 1993, pp. 445–457.

U.S. Patent Application No. 08/015,684 entitled "Lead Adapter", McEtchin, et al., Feb. 9, 1993, Ventritex, Inc.

"Thin Bipolar Leads: A Solution to Problems with Coaxial Bipolar Designs", Adler, et al., PACE, vol. 15, Part II, Nov. 1992, pp. 1986–1990.

"Suture Induced Lead Deformity", Maloney, III, et al., NASPE Abstract No. 294, PACE, vol. 18, Part II, Apr. 1995, p. 869.

"Initial Experience with a New Co-Radial Bipolar Pacing Lead", Tang, et al., NASPE Abstract No. 296, PACE, vol. 18, Part II, Apr. 1995, p. 869.

*Primary Examiner*—William E. Kamm
*Assistant Examiner*—Kennedy J. Schaetzle
*Attorney, Agent, or Firm*—Steven M. Mitchell; M. Elizabeth Bush; Mark J. Meltzer

[57] ABSTRACT

The present invention is directed toward providing a composite lead body design for pacing and defibrillation leads. This lead body design improves the lead crush resistance in the lead segment that is implanted in the patient's clavicular region, while maintaining good fatigue resistance in the lead segment implanted in the heart. The clavicular segment has a generally flat profile. By flattening the clavicular segment proximal to the venous entry site, the lead will have a lower profile. Also, by substantially co-aligning the conductors within the clavicular segment, the crush resistance of the lead is significantly improved.

26 Claims, 10 Drawing Sheets

CRUSH RESISTANT IMPLANTABLE LEAD

BACKGROUND OF THE INVENTION

1. Field of the Invention

The present invention relates in general to the field of implantable medical devices, and it more particularly relates to a crush resistant lead for use with an implantable cardiac pulse generator for the detection and management of cardiac arrhythmias. The invention more specifically relates to a lead body design for pacing and defibrillation leads. This new design improves the crush resistance in the portion or segment of the lead implanted in the clavicular region, while maintaining significant fatigue resistance in the portion or segment of the lead implanted in the heart.

2. Background Art

The percutaneous infraclavicular subclavian venipuncture has become the most frequently utilized approach for pacemaker and defibrillator lead placement. Clinical evidence suggests that some leads and central venous catheters placed by percutaneous subclavian venipuncture have developed a number of problems that are apparently associated with the costoclavicular region near the superior thoracic aperture. Efforts are being made to understand and explain these problems. Some studies have suggested that work involving heavy activity of the upper extremities could damage implanted catheters or leads, by bony compression or impingement by dense connective tissues, as they pass beneath the clavicle, over the first rib, and into the thorax.

Several investigators have proposed that an overriding clavicle crushes the lead against the first rib with a "pincher-like" action. Other investigators suggested that implantable leads are susceptible to compressive damage when placed by subclavian venipuncture due to soft tissue entrapment rather than bony contact. Yet other studies recommended that percutaneous subclavian venipuncture be abandoned in some cases because the incidence of lead fracture in the costoclavicular region is unacceptable.

Some of the foregoing studies are illustrated in an article entitled "Anatomical and Morphological Evaluation of Pacemaker Lead Compression" by D. M. Jacobs et al., PACE, volume 16, March, Part I, 1993, pages 434–444; and in another article entitled "Anatomical Mechanisms Explaining Damage to Pacemaker Leads, Defibrillator Leads, and Failure of Central Venous Catheters Adjacent to the Sternoclavicular Joint" by J. E. Magney et al., PACE, volume 16, March, Part I 1993, pages 445–457. The authors of the Jacobs et al. article concluded their study by recommending that the costoclavicular angle be avoided completely, either by placing the lead percutaneously into the axillary vein lateral to the costoclavicular ligament complex or by insertion through the cephalic vein. The authors also added that new methods of percutaneous access need to be developed to consistently and safely cannulate the axillary vein in its more lateral extrathoracic position.

The authors of the Magney et al. article summarized their analysis by suggesting that percutaneous subclavian venipuncture be modified to effect entry into the subclavian vein near the lateral border of the first rib, in order to avoid possible entrapment in soft tissues associated with the clavicle. The authors then recommended alternative methods for effecting such procedure.

The foregoing two articles are representative of the trend of the art in the relevant technological field, and basically recommend a departure from well known and tested procedures for failure to identify an adequate solution to the lead fracture caused by compressive forces in the clavicular region. The recommended changes in implantation technique have been shown to reduce the incidence of lead failure due to mechanical interactions in this region. However, in some patients, these more lateral approaches may be unsuitable, due to small cephalic vein size, for example. Also, it is desirable to have a lead body that has superior crush resistance. Such a lead body will further reduce the incidence of crush and provide a greater safety margin for all patients, regardless of the surgical approach used to implant the leads.

Therefore, it would be desirable to have a new lead body with improved crush resistance in the clavicular region, and fatigue resistance in the heart region. It would also be desirable to have a new sleeve adapted to be selectively fitted over the lead body passing through the clavicular region, for improving the crush resistance characteristic of the lead.

One attempt to address the crushing of implanted leads passing through the clavicle and the first rib is briefly described in U.S. Pat. No. 5,246,014 to Williams et al. This patent discloses a lead system comprised of a lead, an introducer and a guide catheter. The lead has a small diameter body to fit the clearance between the clavicle and first rib, in order to prevent crush fracture. This diameter reduction is accomplished by providing an external introducer for applying torque to screw the lead into the endocardium, thereby obviating the need for a stylet lumen through the lead. However, this patent does not seem to describe a crush resistant multiple conductor lead.

Therefore, it would be desirable to have a new crush resistant multiple conductor lead that is adapted for implantation intra-cardially and in the clavicular region.

Another less common cause for lead crushing is the overtightening of the suture onto the lead body. Therefore it would be desirable to have a new lead design which substantially minimizes lead crushing resulting from suture overconstriction.

SUMMARY OF THE INVENTION

The present invention is directed toward optimizing the construction of an implantable lead, catheter, or other medical leads. In particular, the present invention is directed toward improving the lead crush resistance in the clavicular region of the body, while retaining its fatigue resistance in the heart region.

It is a further object of the present invention to provide a new crush resistant lead comprising multiple conductors, and adapted for implantation intra-cardially and in the clavicular region.

It is another object of the present invention to have a new lead design which substantially minimizes lead crushing resulting from suture overconstriction.

It is still another object of the present invention to provide a new sleeve adapted to be selectively fitted over the lead body passing through the clavicular region, for improving the crush resistance characteristic of the lead.

Briefly, the foregoing and other objects of the present invention are realized by a new composite lead body design for pacing and defibrillation leads. This lead body design improves the crush resistance of the lead in the segment of the lead implanted in the clavicular region of the patient, while maintaining good fatigue resistance in the segment of the lead implanted in the heart.

The clavicular segment has a generally flat profile. By flattening the clavicular segment proximal to the venous entry site, the lead will have a lower profile, thus minimizing raised ridge sensation through the skin, and reducing the likelihood for lead manipulation by the patient and cosmetic concerns. Additionally, by substantially co-aligning the conductors within the clavicular segment, the crush resistance of the lead is significantly improved.

In one embodiment, the clavicular conductors include a coil conductor that defines a central styler lumen, and which is interposed between two solid conductors for added physical support and crush resistance.

In another embodiment, the clavicular segment includes a plurality of suture holes that extend throughout the height of the clavicular segment, such that one suture hole is positioned on each side of a solid conductor.

In still another embodiment, the lead includes a connector assembly for modularly interconnecting the clavicular segment and the cardiac segment. The connector assembly includes a sleeve that fits over the clavicular segment for providing a fluid tight seal around the connector assembly.

In a further embodiment, the lead body defines a stop edge. An expanded polytetrafluoroethylene (ePTFE) sleeve abuts against the stop edge, and tubularly, coaxially covers the clavicular segment for enhancing its crush resistance.

In another embodiment a multi-layered lead body is disclosed. The lead body includes an inner electrical conductor and a plurality of interleaved ePTFE layers and layers of impervious insulation, that tubularly, coaxially cover one or more electrical conductors.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENT

Figure 1:
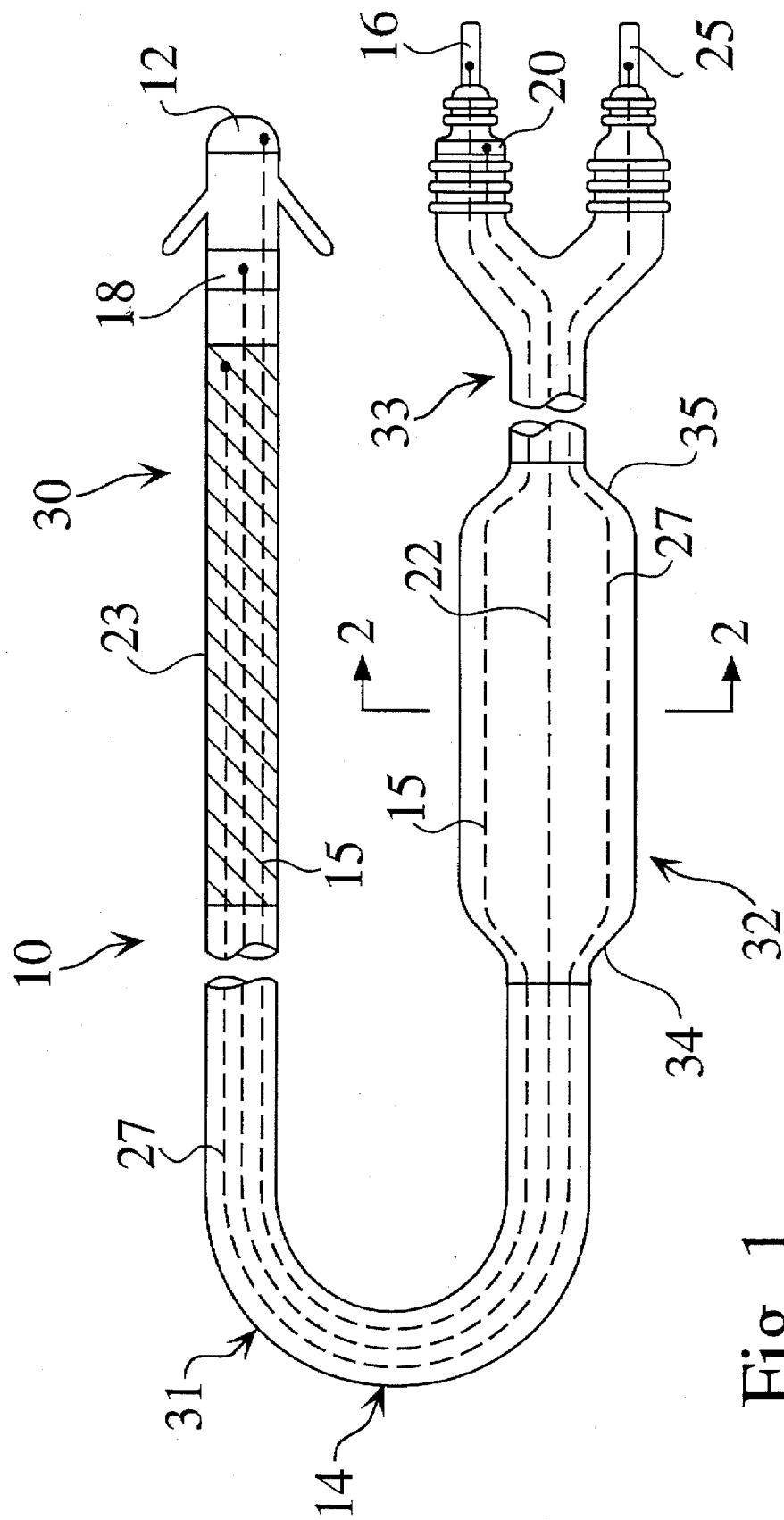
FIG. 1 is a schematic view of a first lead embodiment according to the present invention.

Referring now to the drawings, FIG. 1 illustrates a first embodiment of a lead 10 according to the present invention. Lead 10 is a right ventricular transvenous defibrillation lead with a dedicated sensing electrode. It includes a tip electrode 12 mounted at the distal end of an elongate flexible lead body 14, and coupled to a conductor 15, which, in turn, is electrically connected to a connector 16. A dedicated sensing electrode 18 typically includes a ring electrode that encircles part of lead body 14, a short distance from tip electrode 12. Ring electrode 18 forms a bipolar sensing electrode pair with tip electrode 12, and is coupled to a connector 20 through conductor 22.

An elongated large surface area defibrillation or cardioversion electrode 23 is coupled to a connector 25 through a conductor 27. Electrode 23 takes the shape of a space wound coil, wrapped around lead body 14, and extends for a preset axial distance therealong. Electrode 23 may, for instance, form a "coiled coil". This axial distance is selected such that the proximal end of electrode 23 generally terminates in the vicinity of the tricuspid valve when the distal tip of lead 10 is secured to the myocardium of the right ventricle (RV) apex. The distal end of the electrode 23 is closely positioned relative to the ring electrode 18. Connectors 16, 20 and 25 allow the coupling of lead 10 to the circuitry of an implanted pulse generator, such as disclosed in U.S. Pat. No. 5,007,422 to Pless et al. which is assigned to the assignee of the present invention and which is incorporated herein by reference. While lead 10 is shown in FIG. 1 as a right ventricular transvenous defibrillation lead with dedicated bipolar sensing, for illustration purpose only, it should be understood to a person of ordinary skill in the art that the inventive design may be used universally with most implantable leads that pass through different regions of the human or animal body, for example, a lead having both RV and superior vena cava (SVC) defibrillation electrodes.

Lead 10 is adapted for implantation in various regions of the body. Each of these regions demands specific characteristics for lead 10. For this purpose, lead 10 includes several segments, each of which is individually adapted to meet the requirements of the various body regions in which individual segments of lead 10 are implanted. In the present illustration, lead 10 is designed to withstand compressive forces in the clavicular region (not shown), and fatigue in the heart region (not shown).

To this end, lead body 14 comprises at least three segments. The first segment includes a distal or cardiac segment 30 that extends inside the heart below the tricuspid valve, and also a predetermined distance into a transition zone 31 above the tricuspid valve. This transition zone is located such that the first segment will extend through the tricuspid valve and such that the second segment will extend completely through the venous entry site and the clavicular crush zone, regardless of the size and anatomy of the patient. Cardiac segment 30 has a generally circular cross-section. It is fatigue resistant in order to withstand the heart flexure movement, and is constructed of an elongated, flexible dielectric material, for example silicone rubber or polyurethane. Conductors 15, 22, and 27 extending inside cardiac segment 30 can assume various configurations, for instance they can be coaxial or coradial, as is typical for pacing and defibrillation leads. As used herein, coradial refers to a multifilar conductor coil arrangement, wherein at least some of the wires within the coil are of opposite polarity (or otherwise at different potentials), and insulated from each other.

The second segment includes a proximal or clavicular segment 32 that extends from the transition zone 31, through the venous entry site and the clavicular crush zone, between a first edge 34 and a second edge 35. It has a low profile, and a generally flat, thin construction. Conductors 15, 22, and 27 residing within clavicular segment 32 ("clavicular conductors") may be spaced apart and placed side by side in a substantially co-linear arrangement (in cross-sectional view). These conductors 15, 22, and 27 may be of a coil, cable or other construction, and any combination of conductor structures may be used. Any coil lumen may be optionally filled with a supporting material, for example a cable, or polymer beading.

Figure 12:
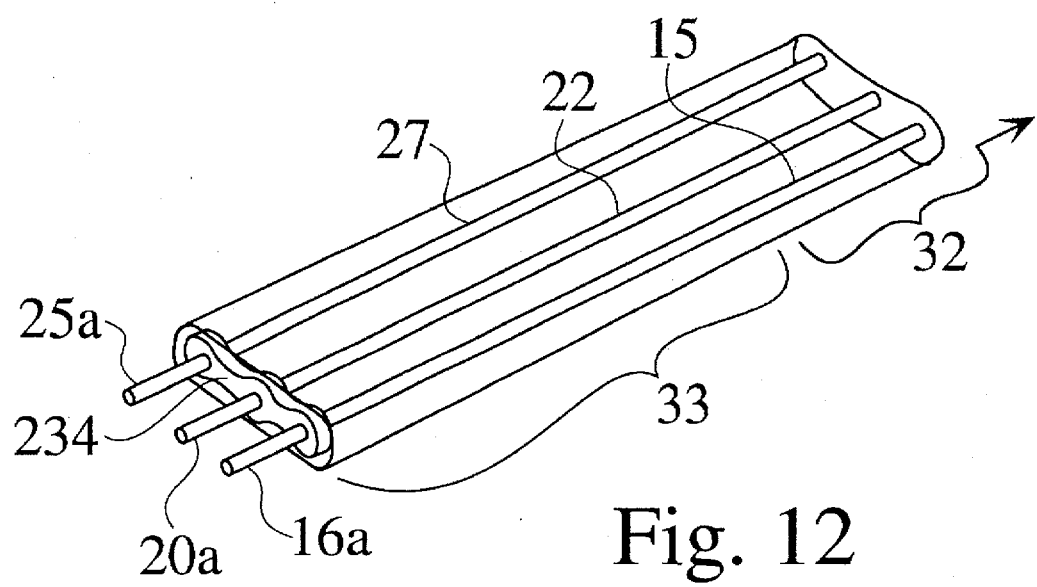
FIG. 12 is a view of a lead embodiment having the connector segment similar in profile to the clavicular segment.

The third segment of lead body 14 includes a conventionally designed lead extension segment 33 that extends from clavicular segment 32 to connectors 16, 20, and 25. This third segment may be of a bifurcated (or trifurcated, etc.) lead body construction, terminating in "standard" type connectors, as shown in FIG. 1. Alternatively, this third segment may share the same low profile, generally flat structure as the second segment, as shown in FIG. 12.

Figure 2:
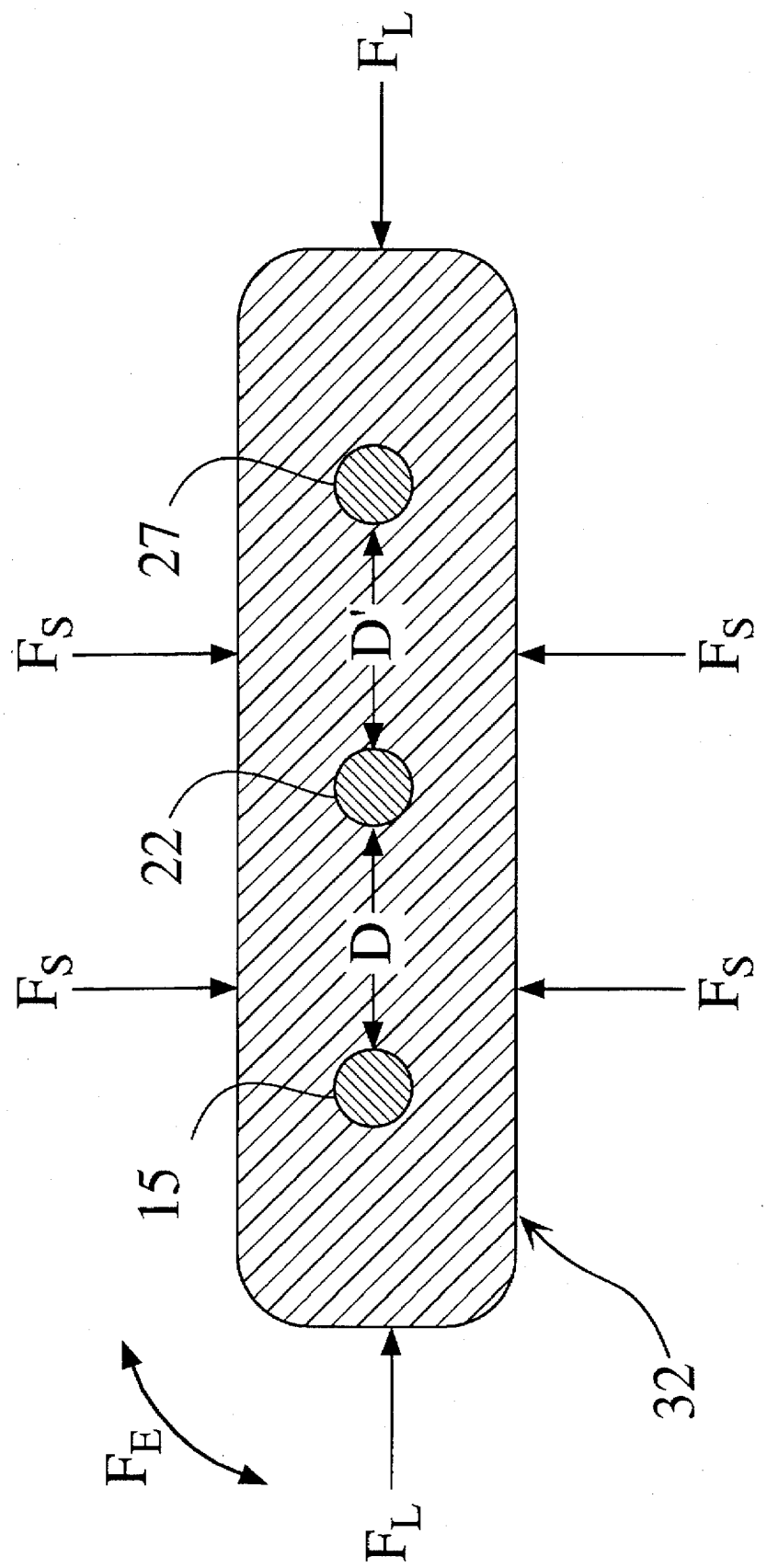
FIG. 2 is a cross-section view of a clavicular segment forming part of the lead of FIG. 1.

By flattening clavicular segment 32 proximal to the venous entry site, lead 10 will have a lower profile, thus minimizing raised ridge sensation through the skin, and reducing the incidence of lead manipulation by the patient and cosmetic concerns. Additionally, by substantially co-aligning conductors 15, 22, and 27, clavicular segment 32 is rendered crush resistant, in that the surface compressive forces, indicated by the arrows $F_S$ in FIG. 2, that are applied on clavicular segment 32 do not force conductors 15, 22, and 27 into contact with each other, since they are segregated by separation intervals D and D'. These intervals D and D' are selected so as to maintain adequate insulation and separation between conductors 15, 22, and 27, even when lateral compressive forces $F_L$ are applied to the sides of clavicular segment 32. Therefore, the present lead design will not be damaged by compressive forces when placed by subclavian venipuncture, whether these forces are due to soft tissue entrapment or bony contact.

Figure 3:
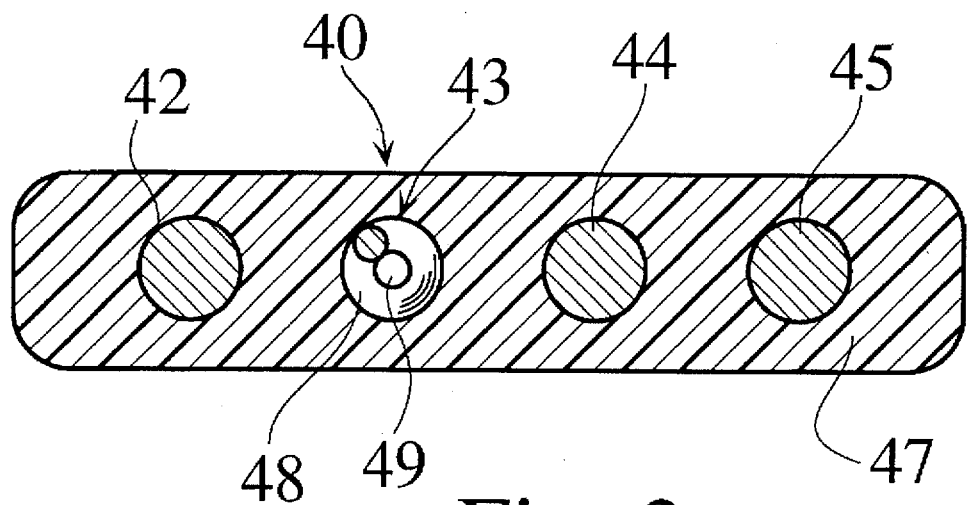
FIG. 3 illustrates a cross-sectional view of a generally flat clavicular segment housing four side-by-side conductors, according to the present invention.

Additionally, the flat row configuration of the clavicular segment can be used to protect an open stylet lumen coil from being crushed by placing it between crush resistant conductors, thus protecting the styler lumen without compromising the lead crush resistance. Alternatively, the coil may be protected by placing it between a crush resistant conductor and a solid strand of nonconductive material such as nylon or nonexpanded polytetrafluoroethylene (PTFE). FIG. 3 illustrates an example of such arrangement, and shows a cross-sectional view of a generally flat clavicular segment 40 housing a plurality of conductors, for example four side-by-side conductors 42, 43, 44, and 45, encased within insulator 47. It should be clear to the person of ordinary skill in the art that conductors 42–45 do not necessarily need to be co-aligned, and that the positions of these conductors 42–45 may be varied provided they are maintained at an adequate separation from each other to avoid crushing.

For illustration purposes only, FIG. 3 shows various types of conductors. For example, conductors 42 and 45 may be solid and used for defibrillation, while conductor 44 may also be solid and used for sensing. As used herein, the term "solid conductor" refers to a conductor of a structure that has no regions substantially lacking in material, and any conductor lumen is filled with a supporting material; thus, such conductors cannot be crushed. The solid conductors 42, 44, and 45 can be solid small diameter wires (as described in U.S. Pat. No. 5,246,014 to Williams et al.), cables, conductors having a cable within a coil (as described in U.S. Pat. No. 5,330,523 to Campbell et al.), or other appropriately selected conductors having no regions substantially lacking in material, such that they are crush resistant. Conductor 43 may be used for pacing, and includes a coil 48 that defines a central stylet lumen 49. Since conductor 43 is disposed between two solid conductors 42 and 44, the latter conductors 42 and 44 will provide sufficient support to the region between them, to protect conductor 43 from being crushed under the compressive forces.

Figure 4:
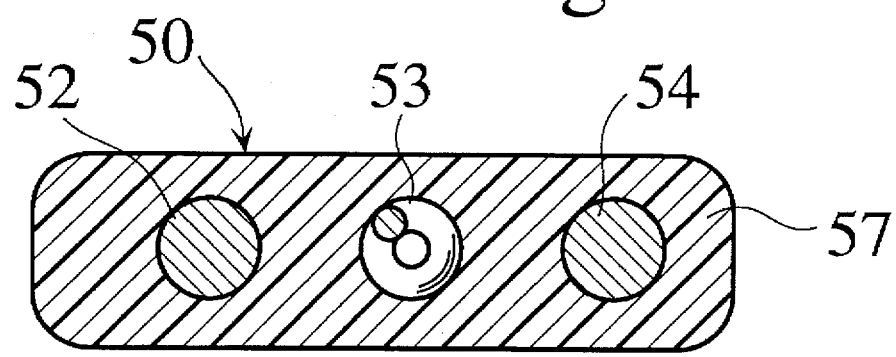
FIG. 4 illustrates a cross-sectional view of another generally flat clavicular segment housing three side-by-side conductors, according to the present invention.

FIG. 4 is a variation of FIG. 3, and shows a clavicular segment 50 with three conductors 52, 53, and 54. Conductors 52 and 54 are similar to conductors 42 and 45 of FIG. 3, and may be used for defibrillation. Conductor 53 is disposed between the two solid conductors 52 and 54 for added physical support and crush resistance. In a specific embodiment, conductor 53 may be a coradial pace-sense conductor. Clavicular segment 50 further includes a generally flat, relatively thin insulator 57, and the geographical centers of conductors 52, 53, and 54 are substantially co-linear (i.e., their axes are substantially coplanar).

Figure 5:
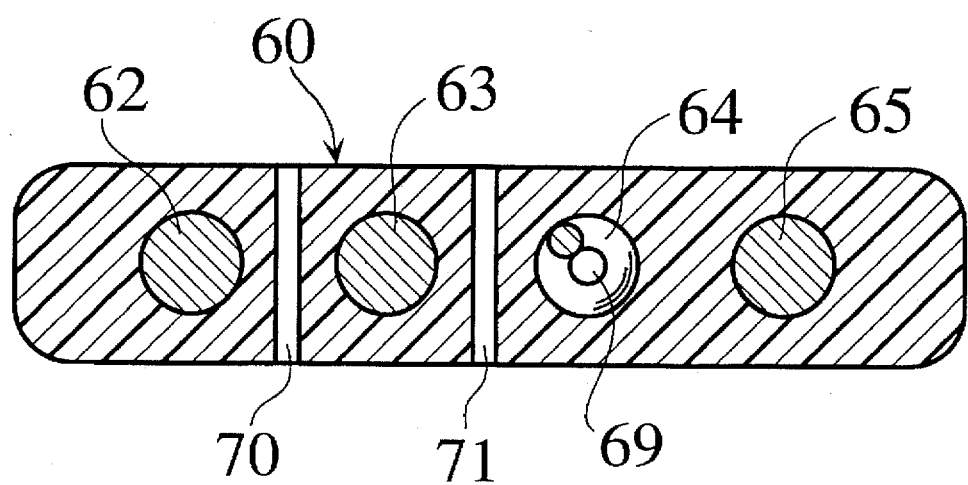
FIG. 5 illustrates a cross-sectional view of yet another generally flat clavicular segment having two suture holes according to the present invention.

FIG. 5 is a cross-sectional view of another clavicular segment 60 according to the present invention. Clavicular segment 60 is generally similar in design and construction to clavicular segment 40, and is shown, for illustration purposes only, to include four conductors 62, 63, 64, and 65.

In the present example, conductors 62, 63, and 65 are solid, while conductor 64 is coiled and defines a central styler lumen 69. As is the case with conductor 43 (FIG. 3) and conductor 53 (FIG. 4), conductor 64 is optionally disposed between two adjacent solid conductors 63, 65, for added support and crush resistance.

Clavicular segment 60 presents an added feature namely a plurality of suture holes, for example suture holes 70 and 71, for anchoring the lead to the vein, around the solid crush resistant conductor 63. Suture holes 70 and 71 are generally parallel to each other, and extend throughout the height of clavicular segment 60.

Figure 6:
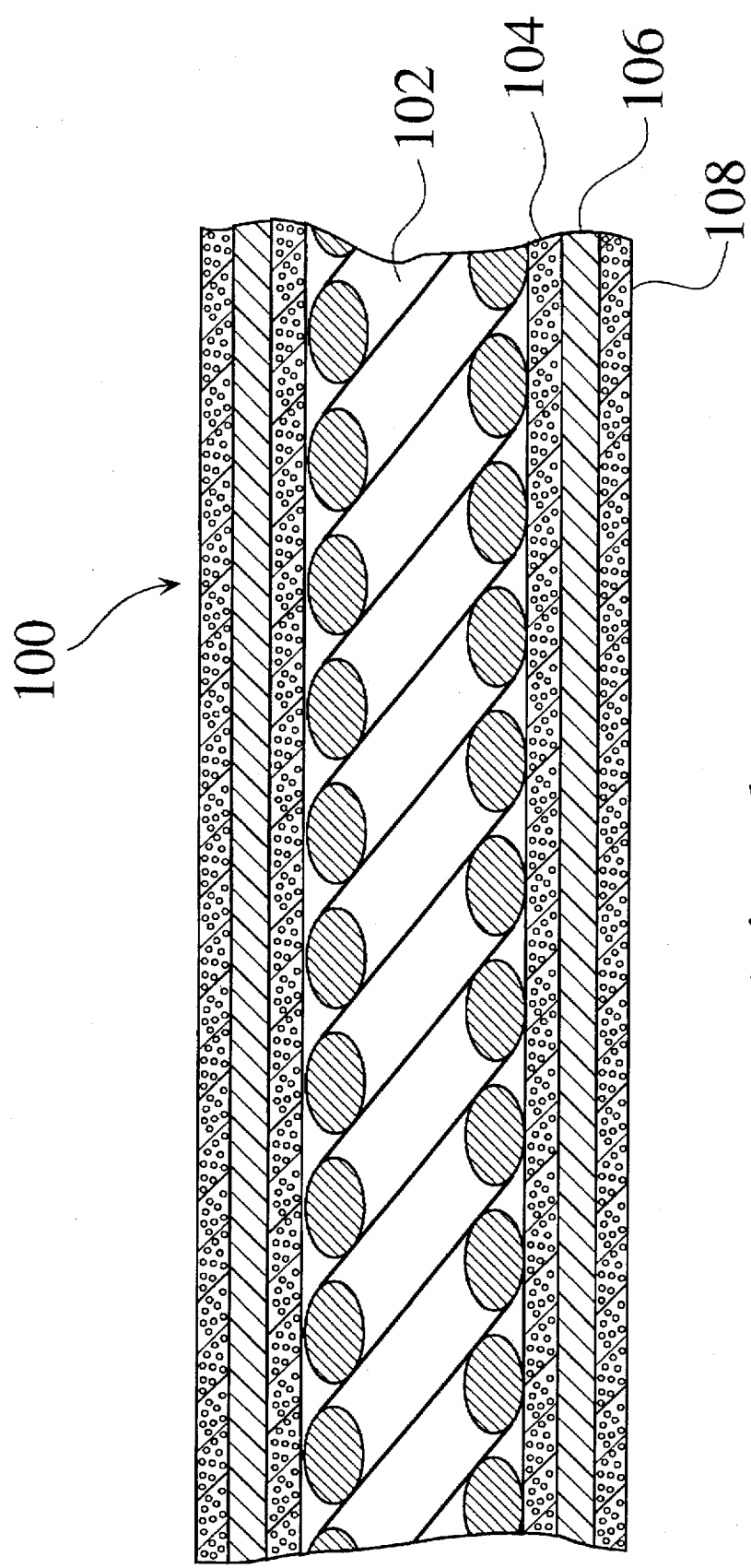
FIG. 6 is an enlarged cross sectional side view of a portion of an implantable lead, such as the lead illustrated in FIG. 1, according to the present invention.

FIG. 6 is an enlarged cross sectional side view of a portion of an implantable lead 100 according to the present invention. An inner electrical conductor 102 is tubularly and coaxially covered with an inner layer of tubing 104 made of expanded polytetrafluoroethylene (ePTFE). An intermediate coaxially oriented tubular layer 106 of impervious insulation, such as silicone rubber, covers inner ePTFE layer 104. This intermediate layer 106 prevents fluids, including body fluids, from reaching conductor 102. Inner ePTFE layer 104 protects intermediate silicone layer 106 from being cut from the inside by conductor 102 whenever pressure is applied to the lead body, for example in the clavicular region or under the ligature at the venous entry site. The exterior surface of intermediate layer 106 is provided with an outer ePTFE layer 108. This porous outer ePTFE layer 108 prevents the silicone layer 106 from being cut from its outside surface by a ligature.

Inner ePTFE layer 104 maintains the flexibility of lead 100 while improving its crush resistance, thus making it appropriate for implantation in various regions of the body, and particularly in the clavicular region, for protection against the damaging effect of compressive forces. Both ePTFE layers 104 and 108 attenuate, absorb and disperse the compressive forces because of the porosity of ePTFE layers 104 and 106, which tend to convert at least part of the radial or compressive forces into lateral or axial forces.

While a coiled conductor 102 is shown in FIG. 6 for illustration purposes only, it should be clear that conductor 102 may assume various other configurations. For example, conductor 102 could be coaxial, cabled or coradial. It should also be understood that the configuration of lead 100 is not limited to the tri-layer configuration and that various portions of the implantable lead could have different configurations. For example purpose only, a lead can have two or more different sections, i.e., a first section that includes a conventional lead design, as disclosed in U.S. Pat. No. 5,044,375 to Bach, Jr. et al., which is incorporated by reference; a second section that includes the flat construction shown in FIGS. 3 through 5; and a third section that includes the construction illustrated in FIG. 6 or a modification thereof.

Figure 7:
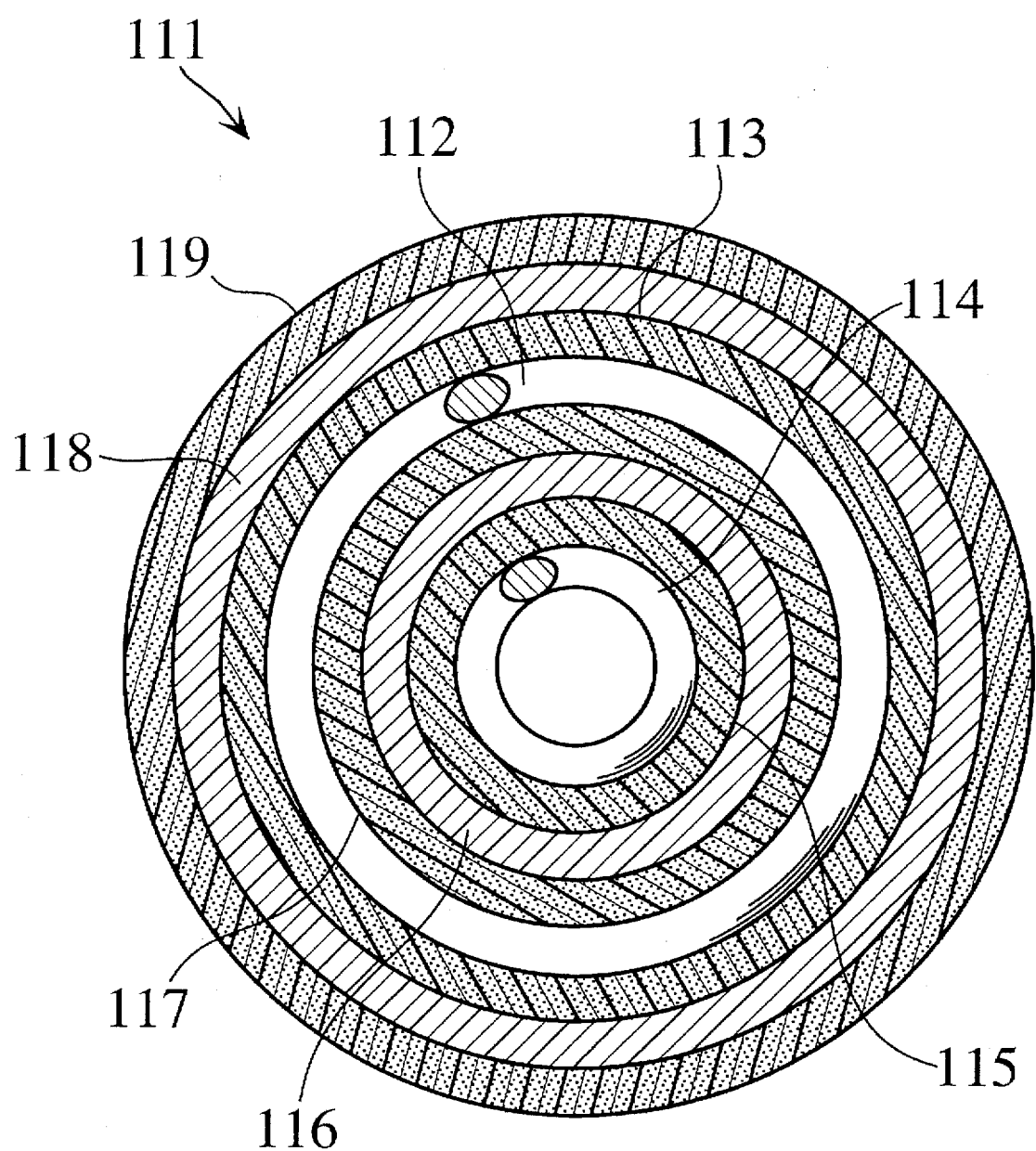
FIG. 7 is a greatly enlarged cross sectional view of another embodiment of a multi-layered lead according to the present invention.

In another embodiment illustrated in cross section in FIG. 7, there is shown a new multi-layered lead or lead section 111. While lead 111 is shown to include two coiled solid-wire conductors 112 and 114, separated by three layers 115, 116 and 117, and surrounded by three layers 113, 118 and 119, it should be understood that a different number or combination of layers is also anticipated by the present invention. Inner conductor coil 114 is similar to inner conductor 102 shown in FIG. 6, and is tubularly and coaxially covered with a first innermost ePTFE layer or tubing 115. In turn, ePTFE layer 115 is covered with a first coaxially oriented tubular layer 116 of impervious insulation, similar to layer 106 shown in FIG. 6. This first impervious insulation layer 116 is covered with a second ePTFE layer 117. Outer conductor coil 112 is covered with an ePTFE layer 113, which, in turn, is covered with a second impervious insulation layer 118, and an outermost ePTFE layer 119 that coats the impervious insulation layer 118.

ePTFE layers 115 and 117 protect electrically insulative layer 116 from being cut by conductor coils 112 and 114 when a force is applied to lead 111, such as from a tight suture, the patient's clavicle, or soft tissue entrapment. Furthermore, if conductor coil 112 were pentafilar, and one wire were to fracture in a lead without the protective ePTFE layers 115 and 117, insulative layer 116 would quickly be cut through by the sharp end of the broken wire. ePTFE layers 115 and 117 are much tougher than layer 116, and may prevent a tear from propagating through to silicone layer 116.

Figure 8:
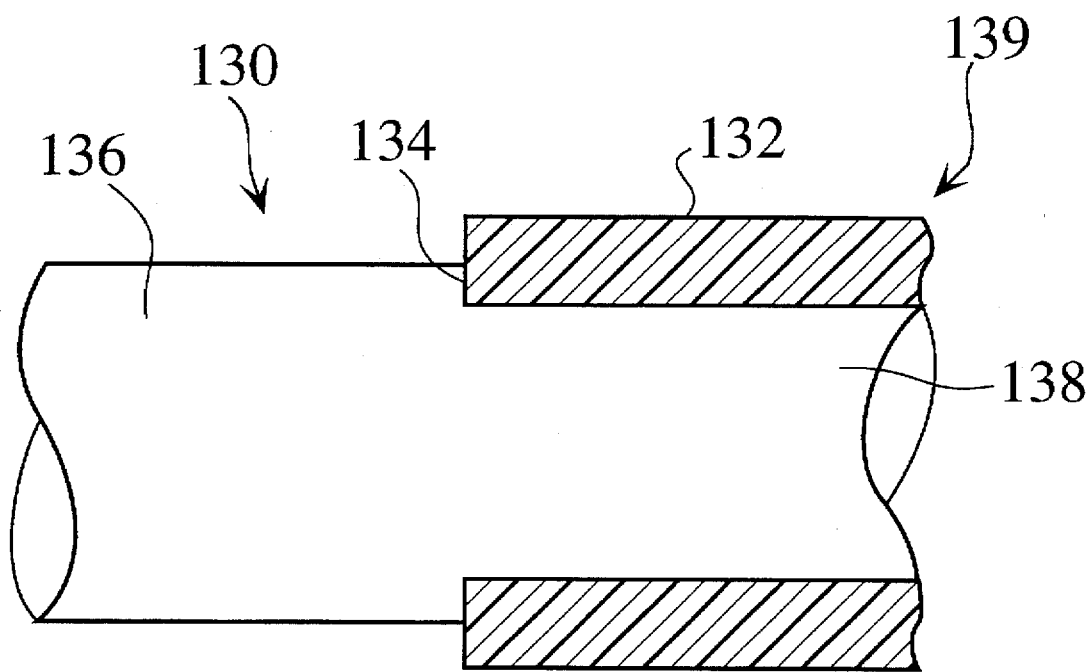
FIG. 8 is a partly sectional view of another embodiment of a lead and a sleeve according to the present invention.

FIG. 8 is a partly sectional view of another embodiment of a lead 130 and a sleeve 132 according to the present invention. Lead 130 can be any conventional lead or one of the leads described herein. In the present embodiment, lead 130 defines a stop edge 134 between a first lead section 136 and a second lead section 138. In the present illustration, the first lead section 136 has a wider diameter than the second lead section 138. Alternatively, lead 130 may be uniform. While stop 134 is shown as a straight or 90 degree-edge, other designs are also anticipated by the present invention. For instance, stop 134 can be conically shaped so that the first lead section 136 tapers smoothly and integrally into the second lead section 138.

Sleeve 132 may be made of ePTFE or a wire braid reinforced plastic or elastomer which enhances the crush resistance of lead 130. In the present example, sleeve 132 is slidably fitted over a selected length of lead 130, which is designed to pass through the clavicular region, and to form a clavicular segment 139. Sleeve 132 may have several alternative outer profiles, such as circular or flat. Additionally, sleeve 132 eliminates the need for a separate suture sleeve, and can be used to anchor lead 130 at the point of venous insertion.

While the embodiments of the present invention are described herein in relation to implantable leads, it should be understood that the same or similar designs can be used in other applications, such as catheters or like medical devices.

Figure 9:
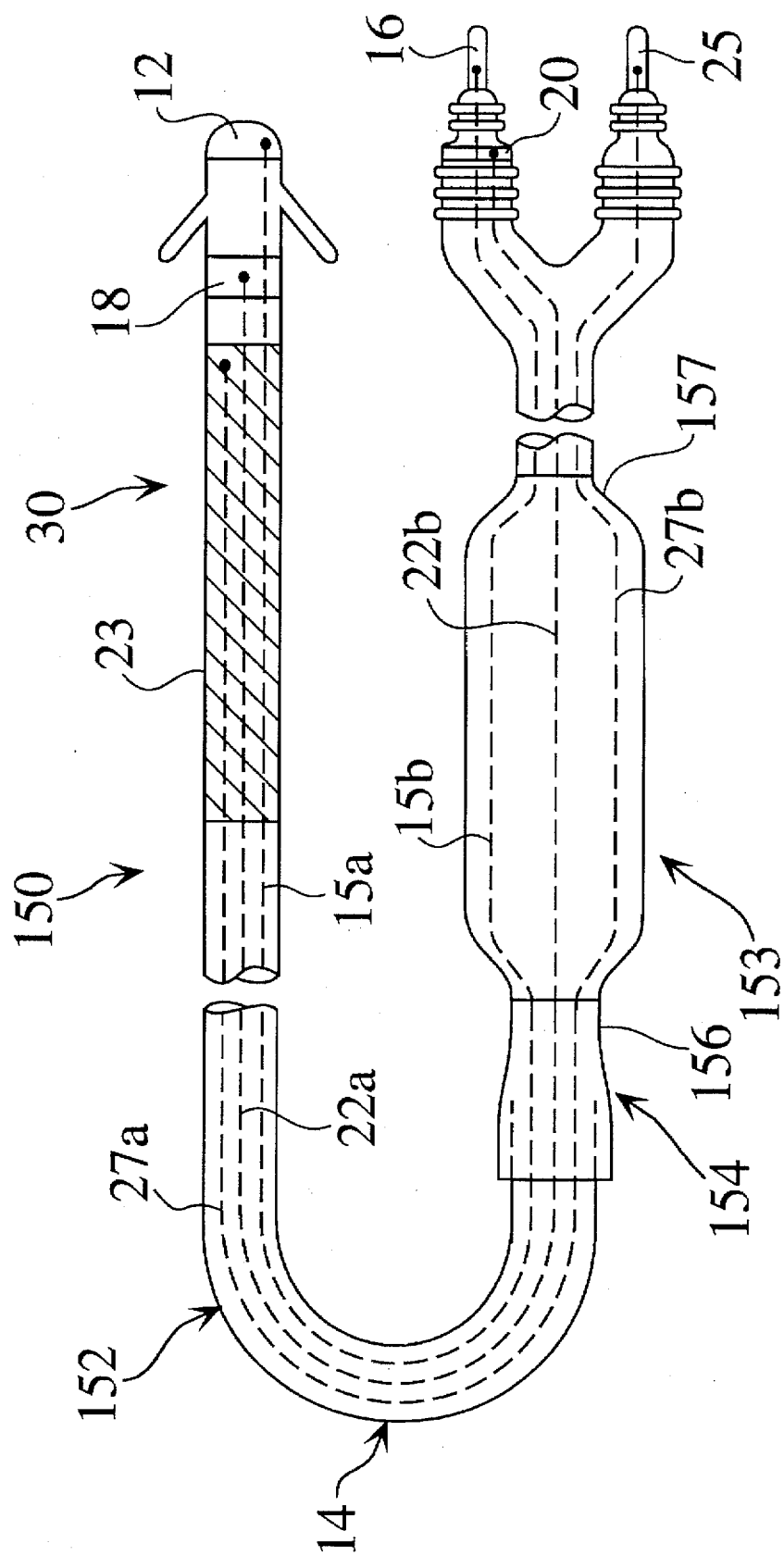
FIG. 9 is a view of a modular, multi-section bipolar lead employing improvements according to the present invention.

FIG. 9 is a view of a new lead 150 employing improvements according to the present invention. Components that are common to the lead embodiment of FIG. 1 are labeled similarly in FIG. 9. In general, lead 150 includes a venous or heart implantable segment 152 and a clavicular segment 153 that are interconnected by means of a connector assembly 154. As described previously, venous segment 152 and clavicular segment 153 have different configurations. For example purpose only, venous segment 152 may have a circular cross-section and defines a central stylet lumen, while clavicular segment 153 may have a generally flattened profile without the styler lumen.

In use, when lead 150 is to be implanted, venous segment 152 and clavicular segment 153 are separate and not joined by connector assembly 154. Venous segment 152 is first implanted and positioned in the heart, using a stylet (not shown). The stylet is then removed, and venous segment 152 is connected to a distal end 156 of clavicular segment 153 by means of connector assembly 154. While only one connector assembly 154 is shown, it should be clear that more than one connector assembly may be used. For instance, another connector assembly (not shown) may be connected to a proximal end 157 of clavicular segment 153 for connection to an extension lead or for other design reasons.

In the present example, lead 150 includes three conductors 15, 22, 27 (FIG. 1), each of which is comprised of two, or at least two sections.

Conductor 15 is comprised of a venous or heart section 15a and a clavicular or pulse generator section 15b, Similarly, conductor 22 is comprised of a venous or heart section 22a and a clavicular or pulse generator section 22b; and conductor 27 is comprised of a venous or heart section 27a and a clavicular or pulse generator section 27b.

Figure 10:
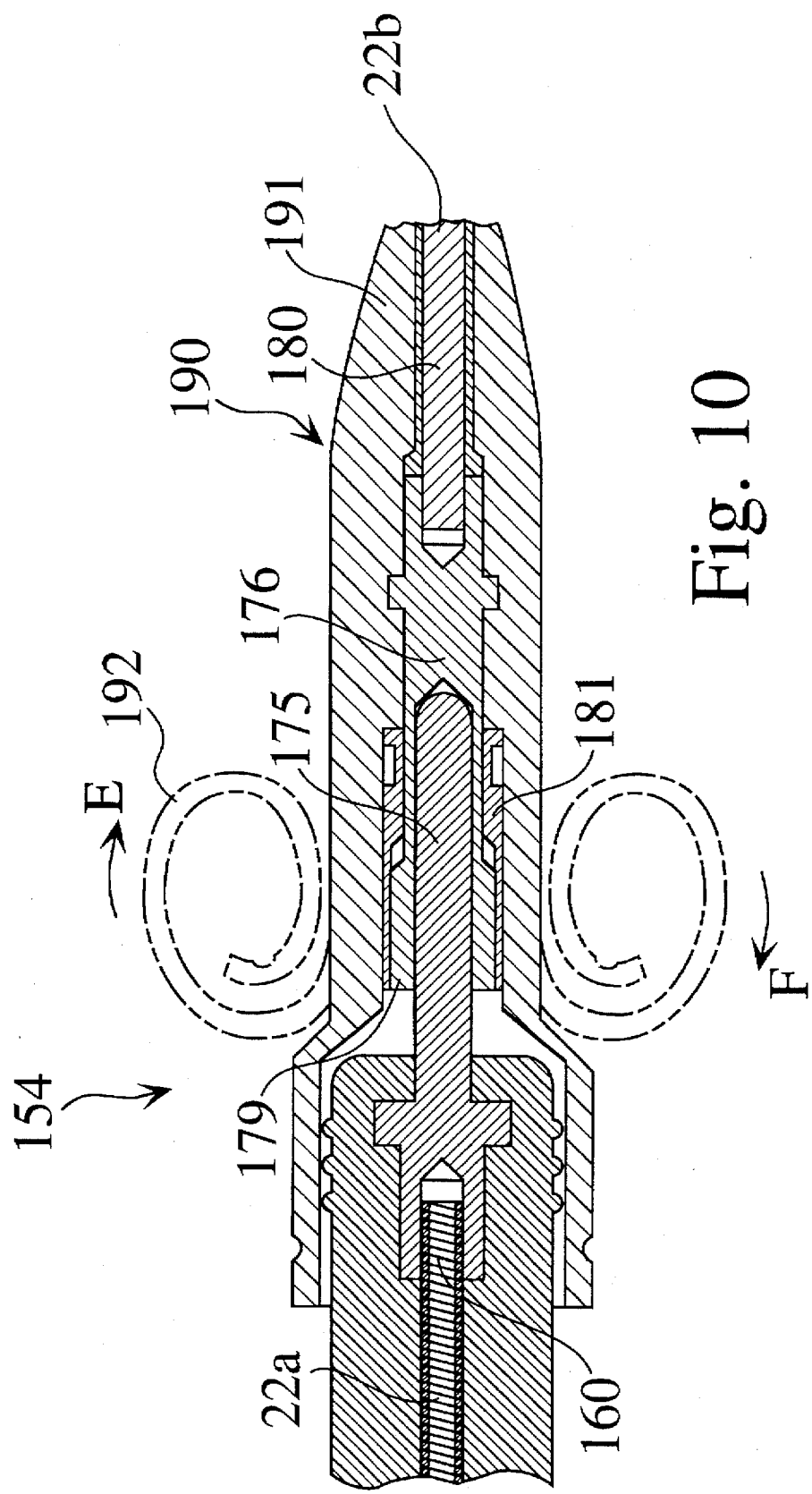
FIG. 10 illustrates a connector assembly partly illustrated in cross-section, for use with the lead of FIG. 9.

Connector assembly 154 is partly illustrated in cross-section in FIG. 10, as joining only one of these three conductors, i.e., conductor 22, for simplicity. It should be understood that the respective sections of the remaining conductors, i.e., 15 and 27 may be joined similarly.

Venous and clavicular sections 22a and 22b, respectively, of conductor 22 can be connected by means of various connector assemblies. While only one connector assembly 154 will be described herein for illustration purpose, it should be understood that other connector assemblies may be used as well. Some of these connector assemblies are described in U.S. patent application Ser. No. 08/015,684, filed on Feb. 9, 1993, to McEtchin et al. entitled "Lead Adapter", and assigned to the assignee of the present invention, U.S. Pat. No. 4,469,104 to Peers-Trevarton, U.S. Pat. No. 4,630,611 to King, and U.S. Pat. No. 5,007,435 to Doan et al., all of which are incorporated herein by reference.

Turning now to FIG. 10, connector assembly 154 and the method of connecting the two conductor sections 22a, 22b are described, in part in the above-referenced McEtchin. A terminal 160 of conductor section 22a is fitted in a connector pin 175 for engaging one end of connector 176. Connector 176 forms part of connector assembly 154, and includes a plurality of longitudinal fingers 179 that are forced inwardly by a compression ring 181. Connector 176 is also electrically connected, at its other end, to a terminal 180 of conductor section 22b. While conductor sections 22a and 22b are shown as having different constructions, i.e., conductor section 22a is represented by a coil, and conductor section 22b is represented by a solid conductor, it should be clear that neither conductor section 22a or 22b is limited to the illustrated configurations. Conductor sections 22a and 22b can be coiled, solid, multifilar, coaxial, coradial or any other adequate conductor.

Connector assembly 154 further includes a sleeve 190 formed of a base member 191 that fits over at least part of terminal 180 of conductor section 22b. Base member 191 extends integrally into a resilient skirt or jacket 192 adapted to provide a fluid tight seal around connector assembly 154.

In use, skirt 192 (shown in broken lines) is rolled back in the direction of arrow E, terminal 180 of conductor section 22b is coupled to connector 176, and skirt 192 is then rolled over the joint or connector 176, in the direction of arrow F, to seal connector assembly 154. The other two pairs of conductor sections (15a, 15b) and (27a, 27b) are similarly connected, and sleeve 190 may cover all three joints.

Clavicular segment 153 and connector assembly 154 can serve a dual function. It can be part of a unitary lead, i.e., lead 150, and it can be used as a lead extension for connection to conventional leads.

Figure 11:
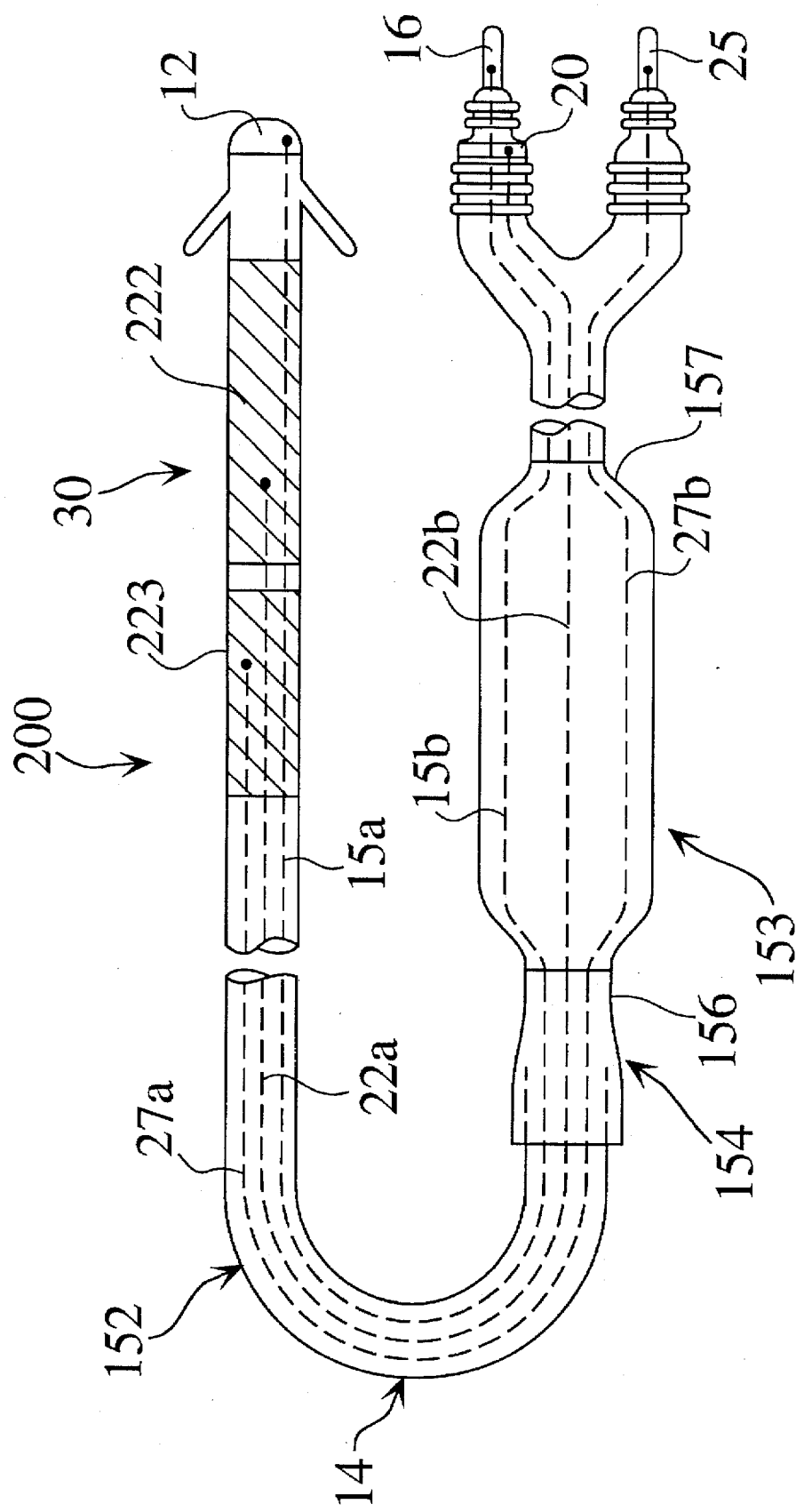
FIG. 11 is view of another modular multi-section lead with integrated sensing, employing improvements according to the present invention.

FIG. 11 is a view of another modular multi-section lead 200. Components that are similar to the lead embodiment of FIG. 9 are labeled similarly in FIG. 11. A main distinction between lead 150 and lead 200 is that the former lead is a right ventricular transvenous defibrillation lead 150 with dedicated bipolar sensing, while the latter lead 200 uses integrated sensing and includes two defibrillation electrodes 222 and 223.

Figure 13:
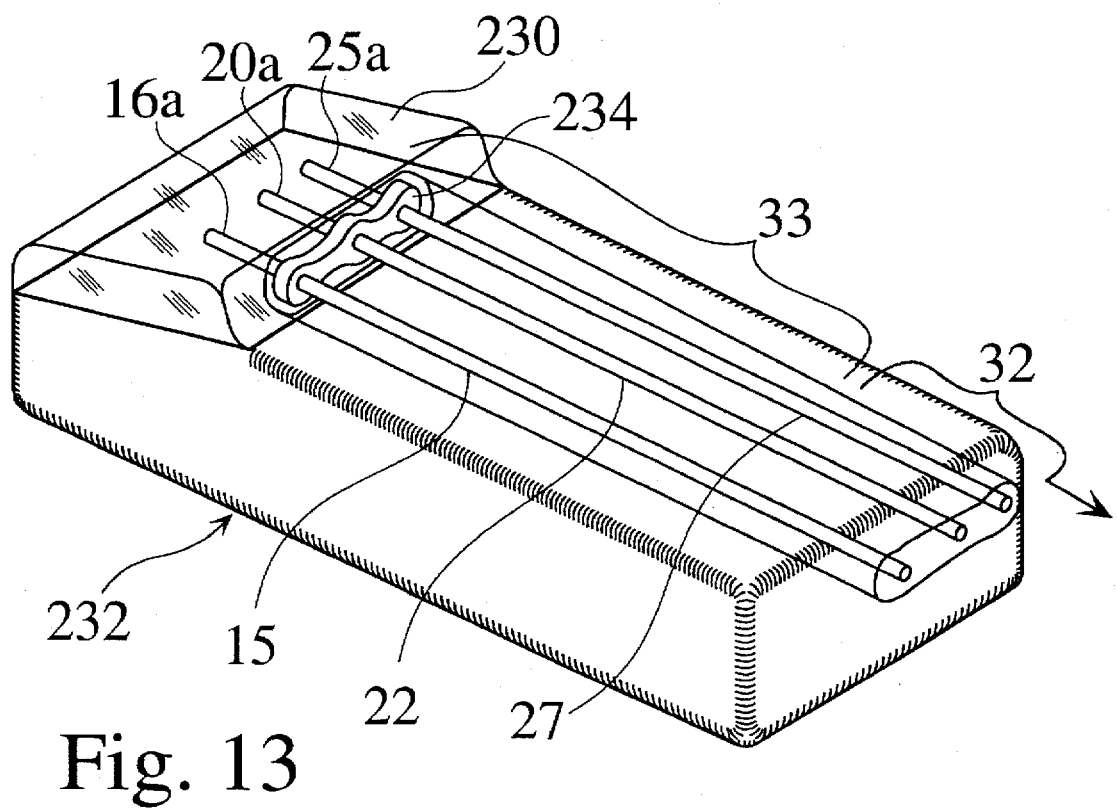
FIG. 13 is a view of the lead embodiment of FIG. 13 plugged into a defibrillator header.

FIGS. 12 and 13 illustrates an embodiment of the invention having a flat, low profile in the third (connector) segment 33, similar in structure to the second (clavicular) segment 32. The conductors 15, 22, and 27 continue through the third segment 33 and terminate in connectors 16a, 20a, and 25a, respectively, which are inserted into a header 230 of a defibrillator 232. Header 230 is designed to accommodate connectors 16a, 20a, and 25a. During installation, all connectors are inserted into the header simultaneously. In the region of segment 33 that ultimately resides within header 230, the connectors 16a, 20a, and 25a may be partially or completely surrounded by rigid plastic 234 to facilitate insertion. A sealing mechanism may be located on the lead or within the header cavity to prevent ingress of body fluids.

The foregoing description of the preferred embodiments has been presented for purposes of illustration and description. It is not intended to be exhaustive or to limit the invention to the precise forms described. Various modifications of the components and methods of use may be employed in practicing the invention. It is intended that the following claims define the scope of the invention, and that the structures within the scope of these claims and their equivalents be covered thereby.

What is claimed is:

1. A medical device at least a part of which being adapted for passing through at least two or more regions of a patient's body, the medical device comprising in combination:

an elongate, flexible body including a cardiac segment and a clavicular segment;

said cardiac segment adapted for insertion in the heart region of the patient's body, and adapted to withstand movement of the patient's heart;

said clavicular segment having a generally low profile, and adapted for insertion in the clavicular region of the patient's body, and adapted to withstand compressive forces in the clavicular region;

a plurality of clavicular conductors that extend through said clavicular segment, wherein said clavicular conductors are spaced apart and generally co-planarly arranged;

wherein said clavicular conductors include at least one coil conductor defining a central stylet lumen and two solid conductors; and wherein said coil conductor is placed between said two solid conductors, for added physical support and crush resistance.

2. The medical device according to claim 1 wherein said cardiac segment has a generally circular cross-section.

3. The medical device according to claim 1 further including a plurality of suture holes extending through said clavicular segment; and wherein at least one of said plurality of suture holes is positioned on each side of one of said two solid conductors.

4. The medical device according to claim 1 further including a pulse generator and at least one lead connector coupled to said clavicular segment and to said pulse generator.

5. The medical device according to claim 4, wherein said pulse generator is a defibrillator.

6. The medical device according to claim 1 and further including a third segment having at least one connector for connecting said third segment to an implantable pulse generator.

7. The medical device according to claim 6, wherein said third segment has a generally flat, thin profile.

8. The medical device according to claim 1, and further including a third segment wherein said third segment is bifurcated and terminates in a pair of connectors for connecting said medical device to a pulse generator.

9. The medical device of claim 1 wherein at least one of said two solid conductors comprises a plurality of solid small diameter wires.

10. The medical device of claim 1 wherein at least one of said two solid conductors comprises a cable.

11. The medical device of claim 1 wherein at least one of said two solid conductors comprises coil having a lumen filled with a supporting material.

12. The medical device of claim 11 wherein said supporting material is a cable.

13. A medical device at least a part of which being adapted for passing through at least two or more regions of a patient's body, the medical device comprising in combination:

an elongate, flexible body including a cardiac segment and a clavicular segment;

said cardiac segment adapted for insertion in the heart region of the patient's body, and adapted to withstand movement of the patient's heart;

said clavicular segment having a generally low profile, and adapted for insertion in the clavicular region of the patient's body, and adapted to withstand compressive forces in the clavicular region;

a plurality of clavicular conductors that extend through said clavicular segment, wherein said clavicular conductors are spaced apart and generally co-planarly arranged; and a connector assembly for modularly interconnecting said clavicular segment and said cardiac segment.

14. The medical device according to claim 13 further including a plurality of cardiac conductors extending through said cardiac segment;

wherein at least one of said cardiac conductors defines a central styler lumen; and wherein at least one of said clavicular conductors is a solid conductor.

15. The medical device according to claim 14 wherein said connector assembly includes a sleeve that fits over at least part of said clavicular segment for providing a fluid tight seal around said connector assembly.

16. A lead extension adapted for implantation in a clavicular region of a patient's body, and for attachment to a lead implantable in another preselected region of the patient's body and including a plurality of lead conductors, said lead extension comprising in combination:

a generally low profile, crush resistant, clavicular segment adapted to withstand compressive forces in said clavicular region;

a connector assembly for modularly interconnecting said clavicular segment and said lead; and said clavicular segment including a plurality of spaced apart, generally co-planarly arranged, clavicular conductors, adapted for connection to corresponding ones of said plurality of lead conductors.

17. The lead extension according to claim 16 wherein at least one of said lead conductors defines a central stylet lumen; and wherein at least one of said clavicular conductors is a solid conductor.

18. A medical device comprising in combination:

an inner electrical conductor coil;

an inner porous insulation layer tubularly covering at least part of said inner electrical conductor coil and coaxial with said coil;

an intermediate coaxially oriented tubular layer of impervious insulation covering at least part of said inner porous layer; and an outer porous layer covering and protecting at least part of said intermediate layer.

19. The device according to claim 18 wherein said porous layers are expanded polytetrafluoroethylene (ePTFE).

20. A medical device comprising in combination:

an inner electrical conductor;

an inner porous insulation layer tubularly, coaxially covering at least part of said inner electrical conductor;

an intermediate coaxially oriented tubular layer of impervious insulation covering at least part of said inner porous layer;

an outer porous layer covering and protecting at least part of said intermediate layer; and at least one other electrical conductor coaxially oriented relative to said inner conductor, and positioned outside said outer porous layer.

21. The medical device according to claim 20 and further including a third porous layer positioned outside said other electrical conductor.

22. A medical device comprising in combination:

an elongate flexible lead body defining a stop edge; and a porous insulative sleeve tubularly, coaxially covering at least part of said lead body, for enhancing its crash resistance, and abutting against said stop edge.

23. The device according to claim 22 wherein said porous insulative sleeve is expanded polytetrafluoroethylene (ePTFE).

24. An implantable lead for connecting an implantable pulse generator to a patient's heart, said lead comprising:

a first distal flexible segment having a generally circular profile for insertion into said patient's heart;

a second proximal segment having a generally flat profile;

a plurality of conductors within said first and second segments and one or more connectors for connecting said conductors at a proximal end of said second segment to said pulse generator, said conductors being in a generally co-planar arrangement in said second segment;

said conductors within said second segment including at least one coil conductor defining a central stylet lumen and two solid conductors; and said coil conductor being placed between said two solid conductors, for added physical support and crush resistance.

25. The lead of claim 24 and further including a plurality of electrodes positioned on said first segment and each connected to at least one of said plurality of conductors.

26. A transvenous lead for use with an implantable pulse generator and implantation into a patient's body comprising:

an elongate, flexible lead body including a distal segment having a generally circular cross-section for placement within said patient's vascular system and heart;

said lead body further including a proximal segment spaced from said distal segment to allow placement in the region of said patient's clavicle and having a generally flat, thin profile relative to said distal segment for resistance to compressive forces in said patient's clavicular region; and said lead body further including a lead extension segment, wherein said proximal segment is positioned between said distal segment and said lead extension segment.

* * * * *